(12) United States Patent
Mauch

(10) Patent No.: US 12,233,221 B2
(45) Date of Patent: Feb. 25, 2025

(54) TELESCOPING CATHETER

(71) Applicant: Medtronic Vascular, Inc., Santa Rosa, CA (US)

(72) Inventor: Kevin Mauch, Windsor, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 211 days.

(21) Appl. No.: 17/086,678

(22) Filed: Nov. 2, 2020

(65) Prior Publication Data

US 2021/0046284 A1 Feb. 18, 2021

Related U.S. Application Data

(63) Continuation of application No. 15/347,037, filed on Nov. 9, 2016, now Pat. No. 10,869,991.

(51) Int. Cl.
*A61M 25/01* (2006.01)
*A61F 2/24* (2006.01)
(Continued)

(52) U.S. Cl.
CPC ........... *A61M 25/01* (2013.01); *A61F 2/2427* (2013.01); *A61F 2/95* (2013.01); *A61M 25/0021* (2013.01);
(Continued)

(58) Field of Classification Search
CPC .............. A61M 5/347; A61M 25/0021; A61M 25/0043; A61M 25/01; A61M 2025/0004; A61M 2025/0006; A61M 2025/0175; A61M 2039/1033; A61M 2/243; A61M 2/2433; A61M 2/2439; A61M 2/958; A61M 2/9661; A61M 2/9662; A61M 2002/9583;
(Continued)

(56) References Cited

U.S. PATENT DOCUMENTS

| 5,120,323 A | 6/1992 | Shockey et al. |
| 5,207,648 A | 5/1993 | Gross |

(Continued)

FOREIGN PATENT DOCUMENTS

| EP | 1419743 | 11/2003 |
| EP | 0773810 | 7/2004 |

(Continued)

OTHER PUBLICATIONS

International Search Report and Written Opinion for PCT/US2017/059353, mailed Jan. 31, 2018, 15 Pages.

(Continued)

*Primary Examiner* — Kami A Bosworth
(74) *Attorney, Agent, or Firm* — Medler Ferro Woodhouse & Mills PLLC

(57) ABSTRACT

A telescoping catheter including an elongated tubular member having a proximal end, a distal end, and a passageway extending between the proximal end and the distal end. The tubular member includes a first tubular segment and a second tubular segment. The first tubular segment and the second tubular segment are slidable relative to one another to vary a length of the tubular member. The first tubular segment includes a first connector mateable with a second connector of the second tubular segment to selectively maintain the first and second tubular segments in an extended position. The second tubular segment includes a second proximal end that is mateable with a handle.

16 Claims, 5 Drawing Sheets

(51) Int. Cl.
  *A61F 2/95* (2013.01)
  *A61M 25/00* (2006.01)
  *A61M 25/06* (2006.01)

(52) U.S. Cl.
  CPC .... *A61M 25/0043* (2013.01); *A61M 25/0662* (2013.01); *A61F 2220/0033* (2013.01); *A61F 2250/0065* (2013.01); *A61M 2025/0006* (2013.01); *A61M 2025/0008* (2013.01); *A61M 2025/0063* (2013.01); *A61M 2025/0175* (2013.01); *A61M 2025/0681* (2013.01)

(58) Field of Classification Search
  CPC ... A61M 2002/9586; A61M 2002/9623; A61F 2/2427; A61F 2/2436; A61F 2/95; A61F 2/9517; A61F 2/9522; A61F 2/954; A61F 2/962; A61F 2/966; A61F 2002/9505; A61F 2002/9665
  See application file for complete search history.

(56) References Cited

U.S. PATENT DOCUMENTS

| | | |
|---|---|---|
| 5,591,143 A | 1/1997 | Trombley, III et al. |
| 5,591,194 A | 1/1997 | Berthiaume |
| 5,658,309 A | 8/1997 | Berthiamume |
| 5,992,899 A | 11/1999 | Strowe |
| 6,589,207 B1 | 7/2003 | El-Nounou |
| 6,837,870 B2 | 1/2005 | Duchamp |
| 7,717,899 B2 | 5/2010 | Bowe et al. |
| 10,869,991 B2 | 12/2020 | Mauch |
| 2003/0078467 A1 | 4/2003 | Whalen et al. |
| 2003/0105451 A1 | 6/2003 | Westlund et al. |
| 2005/0004553 A1 | 1/2005 | Douk |
| 2005/0027236 A1 | 2/2005 | Douk |
| 2006/0212022 A1 | 9/2006 | Gellman |
| 2008/0051821 A1 | 2/2008 | Gephart |
| 2008/0183128 A1 | 7/2008 | Morriss et al. |
| 2008/0255651 A1 | 10/2008 | Dwork |
| 2009/0005741 A1 | 1/2009 | Martin et al. |
| 2009/0137985 A1 | 5/2009 | Tanghoej et al. |
| 2010/0094257 A1 | 4/2010 | Stalker et al. |
| 2011/0224653 A1 | 9/2011 | Torstensen |
| 2012/0168324 A1 | 7/2012 | Carleo |
| 2012/0289972 A1 | 11/2012 | Hofmann et al. |
| 2012/0310138 A1 | 12/2012 | Behan |
| 2013/0172821 A1 | 7/2013 | Potter |

FOREIGN PATENT DOCUMENTS

| | | |
|---|---|---|
| EP | 2522312 | 11/2012 |
| WO | 2008097949 | 8/2008 |
| WO | 2016122862 A1 | 8/2016 |

OTHER PUBLICATIONS

Extended European Search Report issued Dec. 16, 2022 in EP Appl. No. 22196892.8.

TELESCOPING CATHETER

CROSS-REFERENCE TO RELATED APPLICATIONS

This application is a Continuation application of Ser. No. 15/347,037, filed on Nov. 9, 2016, entitled, "TELESCOPING CATHETER," now U.S. Pat. No. 10,869,991, the entire teachings of which are incorporated herein by reference.

BACKGROUND

The present invention relates to a catheter delivery system. More particularly, it relates to a telescoping delivery catheter for passing a working catheter through to a target site.

A wide variety of medical procedures are performed at or within internal bodily vessels, channels, canals, or chambers. Due to the particular procedure and/or to minimize patient trauma, oftentimes the medical device useful for performing part or all of the procedure is introduced through a small incision into the bodily vessel, channel, canal, or chamber in question; or into a bodily vessel, channel, canal, or chamber that is otherwise connected to the site of interest (or target site), and then guided through that vessel to the target site with a guide wire and/or mandrel in a catheter.

Generally, catheters are introduced into tortuous regions of vasculature and to the target site via a conventional guidewire. The guidewire, which is a very thin and typically very flexible in order to traverse the tortuous vasculature and provides a pathway across the target site. A hollow catheter can be advanced over the guidewire to reach the target site. For example, minimally invasive approaches have been developed to facilitate catheter-based implantation of the valve prosthesis on the beating heart, intending to obviate the need for the use of classical sternotomy and cardiopulmonary bypass. In general terms, an expandable prosthetic valve is compressed about or within a catheter, inserted inside a body lumen of the patient, such as the femoral artery, and delivered to a desired location in the heart.

The heart valve prosthesis employed with catheter-based, or transcatheter, procedures generally includes an expandable multi-level frame or stent that supports a valve structure having a plurality of leaflets. The frame can be contracted during percutaneous transluminal delivery, and expanded upon deployment at or within the native valve. The valved stent is crimped down to a desired size and held in that compressed state within a sheath or by other means for transluminal delivery. Retracting the sheath (or other release operation) from this valved stent allows the stent to self-expand to a larger diameter, fixating at the native valve site. In more general terms, then, once the prosthetic valve is positioned at the treatment site, for instance within an incompetent native valve, the stent frame structure may be expanded to hold the prosthetic valve firmly in place.

The actual shape and configuration of any particular transcatheter prosthetic heart valve is dependent, at least to some extent, upon the valve being replaced or repaired (i.e., mitral valve, tricuspid valve, aortic valve, or pulmonary valve). The stent frame must oftentimes provide and maintain (e.g., elevated hoop strength and resistance to radially compressive forces) a relatively complex shape in order to achieve desired fixation with the corresponding native anatomy. Taken in combination, these design features can give rise to delivery obstacles. For example, when compressed and constrained within the delivery device's outer sheath capsule, a self-expanding stent frame will exert significant radial forces on the capsule. Thus, the capsule must have a robust construction, capable of statically resisting the applied force. However, the capsule, as well as other portions of the catheter sheath, must also be sufficiently flexible to traverse the tortuous path leading to the native valve annulus site. As a point of reference, the preferred delivery approach oftentimes includes one or more significant bends or turns. In many instances, the native anatomy creates the "tight" or small radius of curvature bends. In some circumstances, the catheter is too stiff for the native anatomy and causes the anatomy to straighten or be distorted out of its natural orientation. In other circumstances, the catheter is more flexible and as the capsule (or other components of the delivery device) comes into atraumatic contact with the native anatomy, the native anatomy naturally assists in "forcing" the catheter sheath (including the capsule) to the necessary shape.

Other anatomical-based constraints may be placed on the transcatheter delivery system, such as size and/or length. For example, when accessing certain valves via certain approach techniques, deployment of a conventionally-compressed and delivered prosthetic heart valve may be difficult due to anatomical space limitation (e.g., when accessing the mitral valve via trans-septal approach, limited space may be available in the left atrium for locating and manipulating the delivery system in effectuating prosthetic valve deployment). These anatomical constraints can be more difficult to address with larger stented prosthetic valve designs.

The particular delivery catheter, or delivery capsule at the end of the delivery shaft, may not have sufficient rigidity to recapture a deployed intra-bodily medical device, such as a stented heart valve, and to be easily advanced through body vessels, channels, canals, chambers, etc. during deployment to the target site. Attempts to recapture may cause the delivery catheter to buckle or axially compress, while adding rigid "spines" in the catheter to increase axial rigidity can inhibit the catheter's ability to easily navigate through the vasculature. Accordingly, additional rigidity can be added with an outer catheter, in particular as part of a system including a telescoping outer catheter assembled over the delivery catheter readily extendable over the delivery catheter as needed.

SUMMARY

One aspect of the present invention relates to a telescoping catheter including an elongated tubular member having a proximal end, a distal end, and a passageway extending between the proximal end and the distal end. The tubular member includes a first tubular segment and a second tubular segment. The first tubular segment and the second tubular segment are slidable relative to one another to vary a length of the tubular member. The first tubular segment includes a first connector mateable with a second connector of the second tubular segment to selectively maintain the first and second tubular segments in an extended position. The second tubular segment includes a second proximal end that is mateable with a handle.

Another aspect of the present invention relates to a catheter system including an outer catheter member having a proximal end, a distal end, and a passageway extending between the proximal end and the distal end. The outer catheter member includes a first tubular segment telescopingly received within a second tubular segment. The first tubular segment includes a first connector at a first proximal end. The second tubular segment includes a second connector at a second distal end. The first connector is mateable with the second connector to maintain the first and second tubular segments in an extended position. An inner catheter member is slidably received within the outer catheter member and passed through the distal and proximal ends. A handle is coupled to a proximal end of the outer catheter member. The inner catheter member slidably received within the handle.

Another aspect of the present invention relates to a method of using a catheter. The method includes inserting an inner catheter through an outer catheter. The outer catheter including a first tubular segment and a second tubular segment. The first tubular segment telescopingly received within a second tubular segment. The method also includes assembling a prosthetic valve at a distal end of the inner catheter, inserting the prosthetic valve attached into a vascular of a patient, pushing a length of the inner catheter into the vascular, inserting the first tubular segment of the outer catheter into the vascular over the inner catheter, extending the first tubular segment from an interior of the second tubular segment to an extended position, and selectively coupling the first tubular segment with the second tubular segment in the extended position.

DETAILED DESCRIPTION

Figure 1:
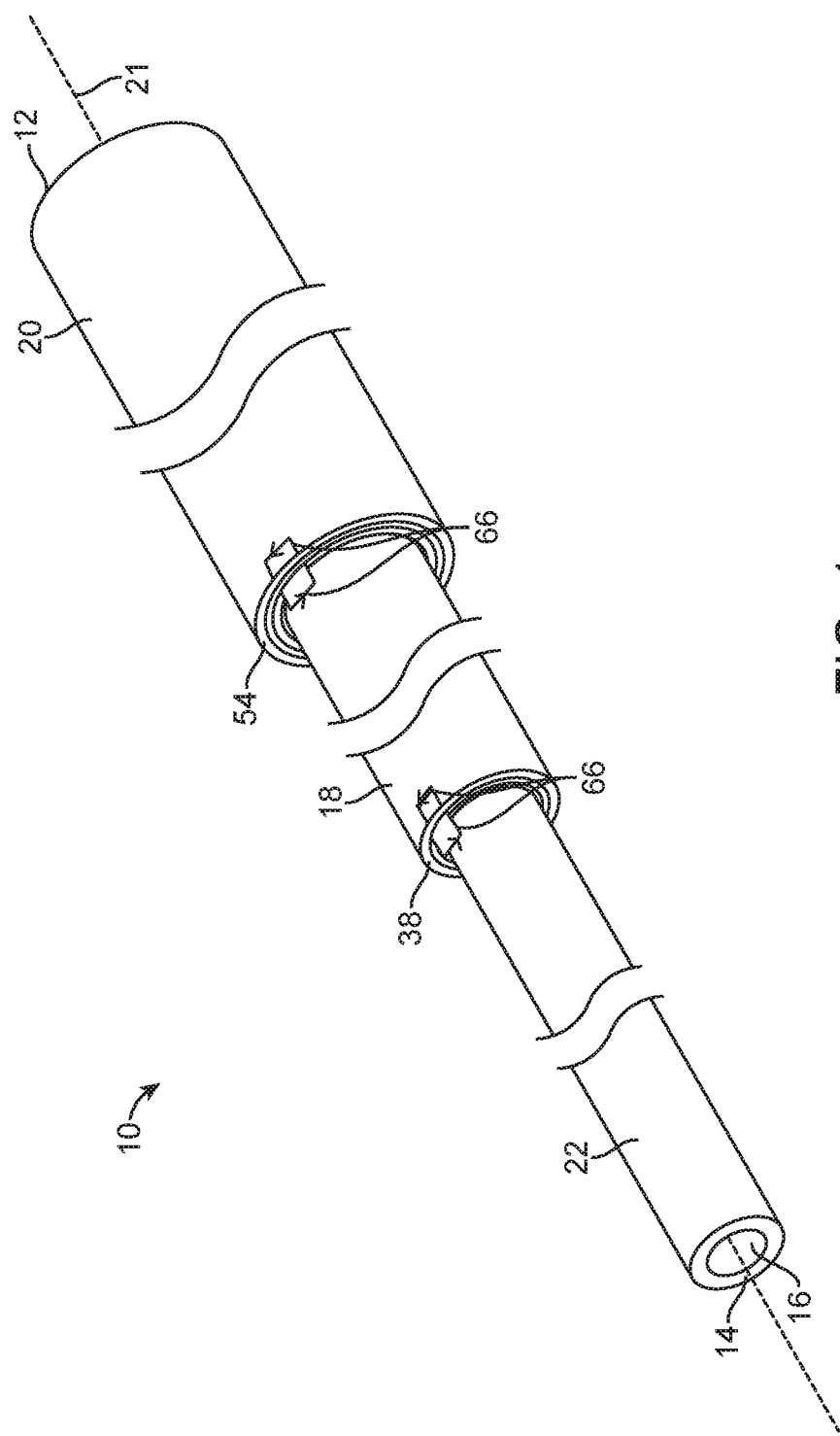
FIG. 1 is a perspective view of a telescoping catheter in accordance with the present invention.

One embodiment of a telescoping catheter 10 in accordance with the present invention is shown in FIG. 1. The telescoping catheter 10 includes an elongated tubular member having a proximal end 12, a distal end 14, and a passageway 16, or lumen, extending from the proximal end 12 to the distal end 14. The telescoping catheter 10 includes at least a first tubular segment 18 and a second tubular segment 20 slidable relative to one another to vary a length of the elongated tubular member along a longitudinal axis, indicated by dashed line 21. The first tubular segment 18 can be slidably received within the second tubular segment 20. In the embodiment illustrated in FIG. 1, a third tubular segment 22, is included along with the first tubular segment 18, the second tubular segment 20 to slidably vary the length of the elongated tubular member of the telescoping catheter 10. Regardless, the telescoping catheter 10 is configured for extending a variable length.

As described further below, the first tubular segment 18 is slidably maintained within the second segment 20 so that a distal end of the first tubular segment 18 can telescope relative to a distal end of the second tubular segment 20. The first tubular segment 18 can be extended or retracted relative to the second tubular segment 20 to control a position of the first tubular segment 18 relative to the second tubular segment 20 along the longitudinal axis and provide an adjustable length of the telescoping catheter 10. The first and second tubular segments 18, 20 can be selectively maintained, or "locked", together when fully extended such that the tubular segments 18, 20 remain in a fully extended position until selectively released, or "unlocked", by the user. In this manner, the extended length of the telescoping catheter 10 is maintained and the first tubular segment 18 is not inadvertently retracted into the second tubular segment 20, as described further below.

Figure 2:
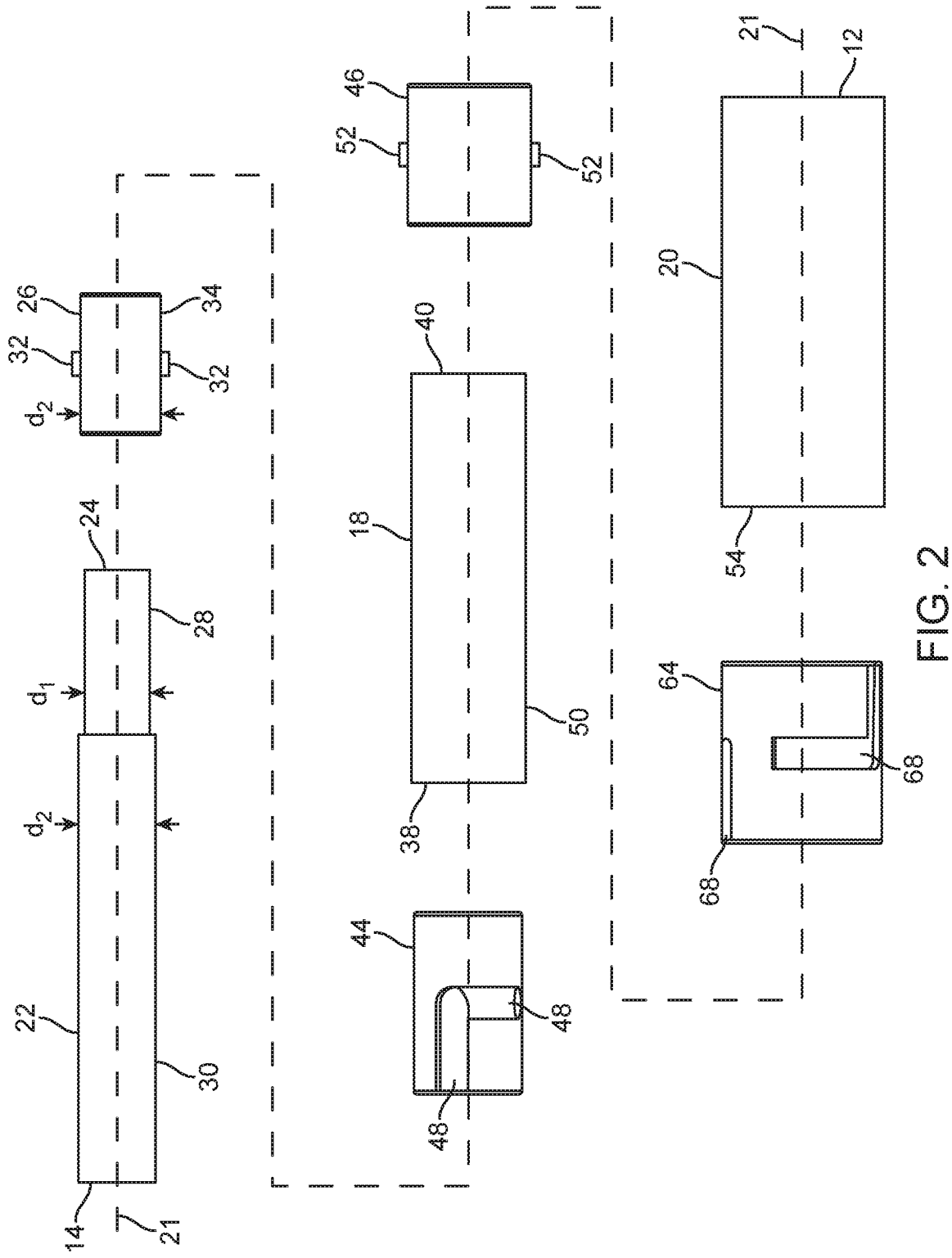
FIG. 2 is an exploded side view of the telescoping catheter of FIG. 1.

With the above in mind, FIG. 2 illustrates an exploded side view of the telescoping catheter 10. FIG. 2 illustrates each of the first, second, and third tubular segments 18, 20, 22 separately. Beginning with the distal-most tubular segment, the third tubular segment 22 includes, and terminates at, the distal end 14 of the telescoping catheter 10. A third proximal end 24 is included opposite the distal end 14. The third proximal connector 26 can be disposed around an exterior surface of the third proximal end 24. A third proximal connector 26 can be positioned at the third proximal end 24 along a portion 28. The portion 28 has a length suitable to accommodate the third proximal connector 26. In one embodiment, an outer diameter "$d_1$" of the portion 28 of the third tubular segment 22 is less than an outer diameter "$d_2$" of a main body 30 to accommodate the third proximal connector 26 and provides that an outer diameter of the third proximal connector 26 is substantially equivalent to the outer diameter "$d_2$" of the main body 30 when joined. The third proximal connector 26 can be adhered or otherwise fixedly coupled to third tubular segment 22. Alternatively, in some embodiments, the third proximal connector 26 can be formed as part of the third tubular segment 22.

In one embodiment, the third proximal connector 26 includes at least one protrusion 32 radially extending from an outer surface 34. The protrusions 32 radially extend a sufficient distance from the outer surface 34 of the third proximal connector 26 to selectively engage within a slotted track, or channel, of a distal end connector 36 as discussed further below. In one embodiment, a pair of protrusions 32 is included and disposed 180° apart on opposite radial sides of the third proximal connector 26.

Figure 3:
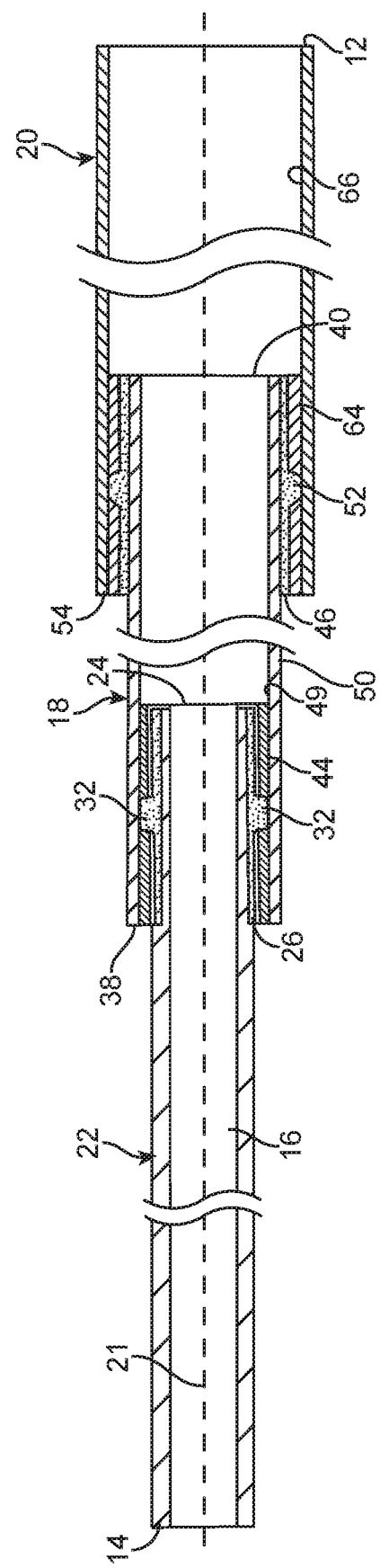
FIG. 3 is a cross-sectional view of the telescoping catheter of FIG. 1.

With continued reference to FIG. 2 and additional reference to FIG. 3, the first tubular segment 18 has a first distal end 38 and a first proximal end 40 opposite the first distal end 38. A first distal connector 44 and a first proximal connector 46 can be disposed at the respective distal and proximal ends 38, 40 of the first tubular segment 18. The first distal connector 44 is configured to be disposed within an interior 49 (see, e.g., FIG. 3) of the first tubular segment 18 and the first proximal connector 46 is configured to be disposed around an exterior 50 of the first tubular segment 18. A thickness of the first tubular segment 18, as measured between the interior 49 and the exterior 50, can be reduced at either one or both of the first distal end 38 and first proximal end 40 to accommodate the distal and proximal end connectors 44, 46 if appropriate. The first distal connector 44 and the first proximal connector 46 can be fixedly attached to the first tubular segment 18 at the respective distal and proximal ends 38, 40 with adhesive or other suitable means. Alternatively, the distal and proximal end connectors 44, 46 can be formed with the first tubular segment 18.

With continued reference to the cross-sectional illustration of FIG. 3, the first distal connector 44 is configured to accommodate the third proximal connector 26 slidably mateable within an interior of the first distal connector 44. The first distal connector 44 includes a channel 48 that the protrusion 32 can be slidably and rotatably insertable into to form a twist-lock style connection. In one embodiment, a pair of channels 48 is oppositely radially disposed on first distal connector 44 to mateably couple with a pair of protrusions 32 on the third proximal connector 26. The first proximal connector 46 is similar to the third proximal connector 26 and can include protrusions 52.

With continued reference to FIGS. 2 and 3, the second tubular segment 20 terminates at the proximal end 12 and includes a second distal end 54 opposite the proximal end 12. A second distal connector 64 can be disposed at the distal end 54 of the second tubular segment 20. The second distal connector 64 is similar to the first distal connector 44. The second distal connector 64 is configured to be disposed within an interior 66 (see, e.g., FIG. 3) of the second tubular segment 20. A thickness of the second tubular segment 18 can be reduced or maintained at the second distal end 54 to accommodate the second distal connector 64. The distal end connector 64 can be fixedly attached to the second tubular segment 20 at the distal end 54 with adhesive or other suitable means. Alternatively, the second distal connector 64 can be formed with the second tubular segment 20.

With continued reference to FIG. 3, the passageway 16 extending from the proximal end 12 to the distal end 14 to the telescoping catheter 10 is suitable to accommodate an inner catheter being slidably disposed therein. Accordingly, as discussed further below with reference to FIGS. 6 and 7, an inner diameter of third tubular segment 22 is sized to accommodate an inner catheter and can be substantially the equivalent between the distal end 14 and the third proximal end 24. More particularly, the inner diameter of the third tubular segment 22 can be slightly larger an outer diameter of the inner catheter to allow the inner catheter to slidably move within the telescoping catheter. Similarly, the inner diameter of the first tubular segment 18 can be similar to and slightly larger than an outer diameter of the third tubular segment 22 in order to slidably accommodate the third tubular segment 22 within the first tubular segment 18 when retracted. In one embodiment, the second tubular segment 20 connected to the handle 204 has an outer diameter of 0.4 inches to 0.5 inches.

In one embodiment, the third tubular segment 22 can have a length greater than a length of the first tubular segment 18 in order to accommodate manual manipulation to longitudinally extend and rotatably couple the first and third tubular segments 18, 22 relative to each other. Similarly, the first tubular segment 18 can have a length greater than the second tubular segment 20 in order to accommodate manual manipulation to longitudinally extend and rotatably couple the first and second tubular segments 20, 22 relative to each other. For example, the tubular segments 18, 20, 22 can include twist-lock style couplings that are rotatably mateable. A variety of other coupling mechanisms can also be used to selectively couple and maintain the tubular segments 18, 20, 22 in an extended position.

As illustrated in FIG. 1, indicators 66 can be included on the exterior surfaces of the tubular segments 18, 20, 22 to indicate positional coupling and alignment of the tubular segments 18, 20, 22, respectively when extended and selectively coupled. The indicators 66 can be markings, for example, visual and/or tactile lines that are adjacently axially aligned when the adjoined tubular segments 18, 20, 22 are coupled in the extended position. In one embodiment, the indicators 66 indicate a beginning and an end of the coupling rotational alignment. The indicators 66 can be included on both the tubular segments to be joined.

Figure 4:
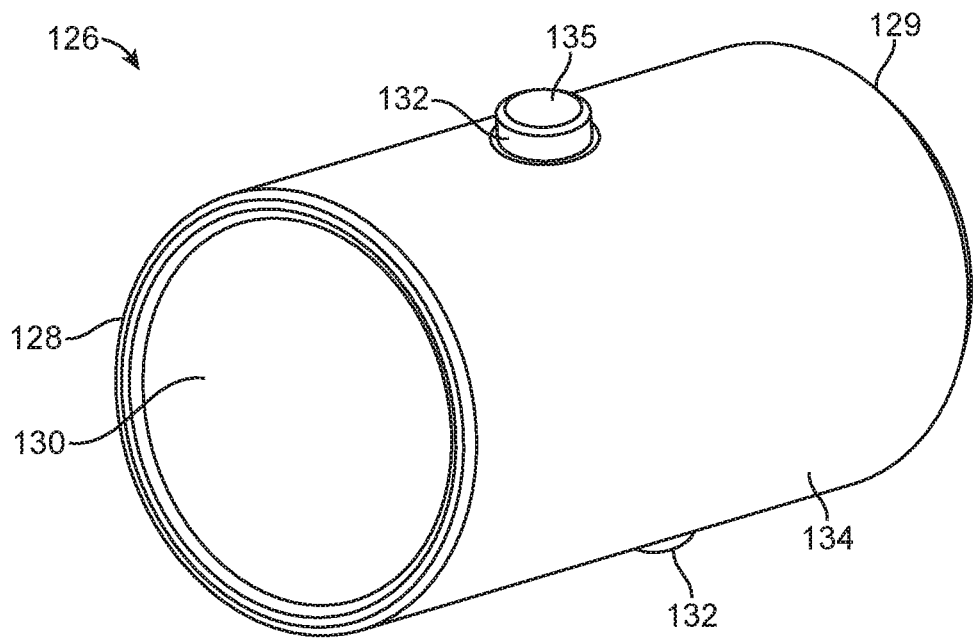
FIG. 4 is an enlarged perspective view of an example proximal connector useable with the telescoping catheter of FIG. 2.

FIG. 4 is an enlarged perspective view of an example proximal connector 126 suitable for use with the telescoping catheter 10. The proximal connector 126 is similar to proximal connectors 26 and 46. The proximal connector 126 is tubular and has opposing ends 128, 129, an interior surface 130, and an exterior surface 134. The proximal end connector 126 includes protrusions 132 radially extending from the exterior surface 134. In one embodiment, two protrusions 132 are including and disposed radially opposite each other (i.e., 180° apart) on the exterior surface 134. In one embodiment, the protrusions 132 are generally disk shaped and has a flattened top surface 135. The protrusions 132 can have a thickness from the exterior surface 134 to the top surface 135 substantially equal to a thickness of a distal connector 144, as described further below.

Figure 5:
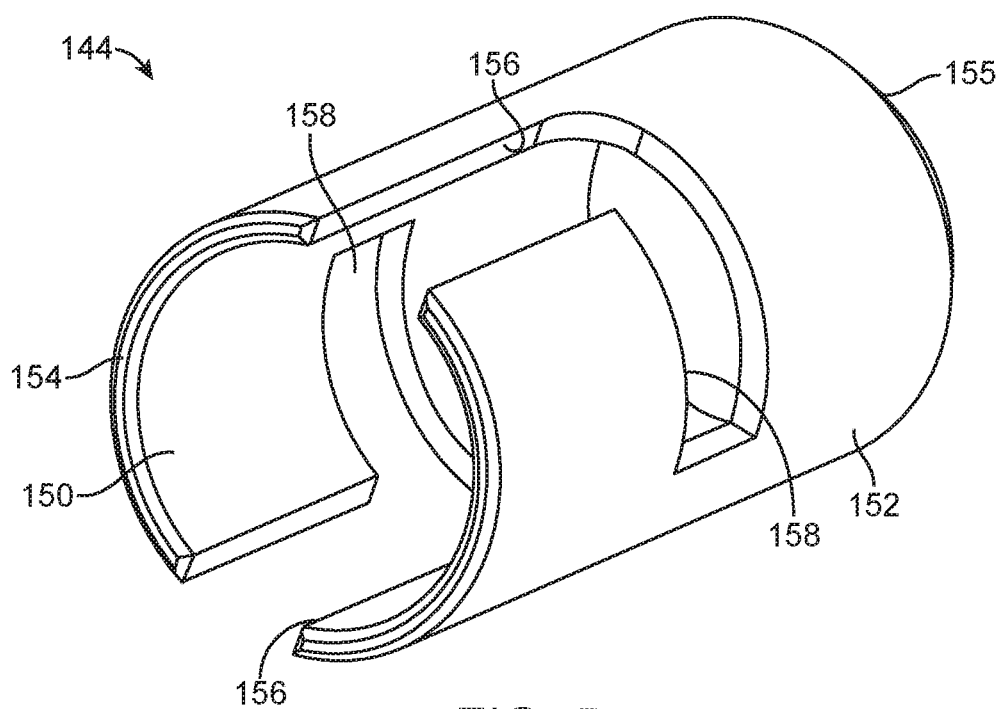
FIG. 5 is an enlarged perspective view of an example distal connector useable with the telescoping catheter of FIG. 2.

FIG. 5 is an enlarged perspective view of an example distal connector 144 mateable with the proximal connector 126. The distal connector 144 is similar to distal connectors 44 and 64. The distal connector 144 is tubular and includes radially opposing channels 148 mateable with protrusions 132 described above. The channels 148 are disposed radially opposite one another as appropriate to engage the protrusions 132 of the proximal connector 126. The channels 148 can extend fully between an interior surface 150 and an exterior surface 152. Each of the channels 148 is open at an end 154 of distal end connector 144 that is disposable at the distal ends 38, 54 of first and second tubular segments 18, 20. The channels 148 include a longitudinal portion 156 and a radial portion 158 perpendicular to the longitudinal portion 156. The radial portions 158 each extend from the longitudinal portions 156 in a first direction such that when the protrusions 132 are inserted into the channels 148 the protrusions 132 are first slidably moved along the longitudinal portion 156 and then turned, or twisted along the radial portion 158 when the proximal and distal end connectors 126 and 144 are joined.

In one embodiment, the radial portions 158 of first distal connector 44 and the radial portions 158 of the second distal connector 64 both extend in the first radial direction. In this manner, the third and first tubular segments 22, 18 and the first and second tubular segments 18, 20, respectively, are engaged in the extended positions by twisting about the longitudinal axis 21 in the same direction. In this manner, the connectors 26, 44 of the third and first tubular segments 22, 18 are not inadvertently disengaged when the connectors 46, 64 of the first and second tubular segments 18, 20 are selectively engaged. The opposing ends 128, 129 and 154, 155 of the proximal end connector 126 and the distal end connector 144, respectively, can include rounded, or beveled, edges to facilitate ease of mating with each other and the tubular segments, as appropriate. The connectors 126, 244 can be formed with, or formed separately and mounted to, interior and exterior surfaces of the mating tubular segments, respectively.

Figure 6:
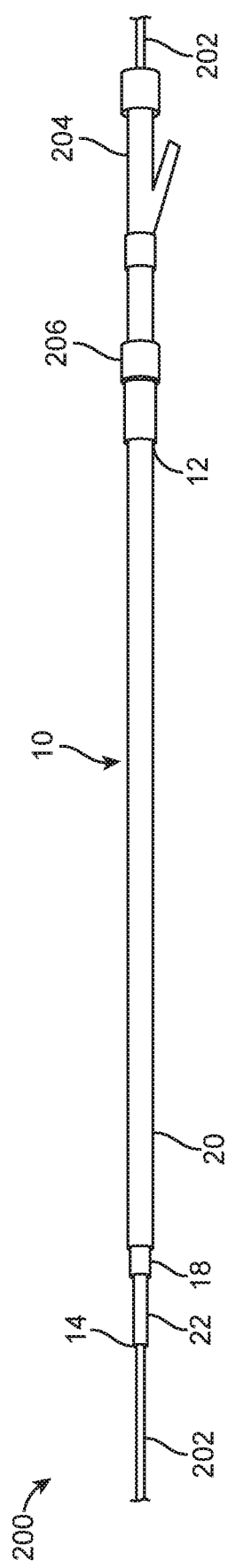
FIG. 6 is a side view of a catheter assembly including the telescoping catheter of FIG. 1 in a retracted state disposed over an inner delivery catheter.
Figure 7:
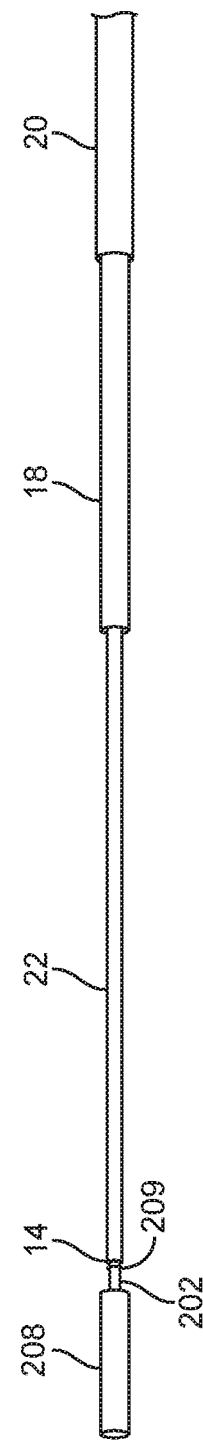
FIG. 7 is a side view of a catheter assembly including the telescoping catheter of FIG. 1 in an expanded state in conjunction with an inner catheter and delivery capsule.

FIGS. 6 and 7 illustrate a catheter assembly 200 including the telescoping catheter 10 disposed over an inner delivery catheter 202. The catheter assembly 200 can include the telescoping catheter 10 as an outer catheter and the inner delivery catheter 202 as a working catheter coaxially disposed within the telescoping catheter 10. The proximal end 12 of the telescoping catheter 10 is coupled to a handle 204 with a luer connector 206, for example. The inner catheter 202 is slidably extendable through and beyond both proximal and distal ends 12, 14 of the telescoping catheter 10. The inner catheter 202 can be coupled to the telescoping catheter 10 at proximal ends of the catheters 202, 10 to "lock" the proximal ends of the catheters together along the longitudinal axis. For example, the inner catheter 202 can be coupled to the telescoping catheter 10 via a hemostatic valve (not shown) in the handle 204.

The telescoping catheter 10 is extendable and retractable over the inner catheter 202 by longitudinally translating, or telescoping, the tubular segments 18, 20, 22 relative to one another. For example, translating the third tubular segment 22 into and out of the first tubular segment 18 and the first tubular segment 18 into and out of the second tubular segment 20. The tubular segments 22, 18 are movable relative to the inner catheter 202 and relative to each other while maintain the tubular segment 20 attached to the handle 204 outside a patient.

More particularly, as described above, the third tubular segment 22 and the first tubular segment 18 are first slidable relative to one another to vary a length of the telescoping catheter 10, with the third tubular segment 22 slidably disposed within the first tubular segment 18, the first and third segments 18, 22 having a retracted position (see, e.g., FIG. 6) and an elongated position (see, e.g., FIG. 7). The first distal connector 26 is mateable with the second proximal connector 44 to selectively maintain the first and second tubular segments 18, 20 together in the elongated position. In this manner, the extended length of the telescoping catheter 10 is maintained and the first tubular segment 18 is not inadvertently retracted into the second tubular segment 20, such as when being pushed into the vascular of a patient or otherwise placed under longitudinal compression. The first and second tubular segments 18, 20 have a similar configuration and arrangement. In this manner, the extended telescoping catheter 10 can be advanced distally coaxially into a patient, and over an inner delivery catheter, for example.

As illustrated in FIG. 6, the tubular segments 18, 20, 22 of the telescoping catheter 10 are "stacked" proximally on a length of the inner catheter 202 in a retracted state. The "stacked" tubular segments 18, 20, 22 are positioned to extend outside a patient with a proximal end 12 of the telescoping catheter 10 coupled to a handle 204. When the inner catheter 202 needs increased rigidity, the telescoping tubular segments 18, 20, 22 are advanced one by one, beginning with the innermost and distalmost tubular segment 22, over the inner catheter 202 into the vasculature. In one embodiment, the inner catheter 202 is a flexible transcatheter mitral valve replacement (TMVR) catheter that can be deliverable over a guide wire. The inner catheter 202 can be configured to deliver a prosthetic valve, for example. If recapture of a partially deployed prosthetic valve is desired, for example, the tubular segments 18, 20, 22 of the telescoping outer catheter 10 can be advanced and selectively interconnected, or coupled together, from outside a patient coaxially over the inner catheter 202 until the tubular segment 22 is just proximal of the valve capsule 208. In one embodiment, a stop 209 is disposed on the inner catheter 202 proximal of the valve capsule 208. The stop 209 extends from the outer diameter of the inner catheter to block, or interface with, the distal end 14 of the telescoping catheter 10. If recapture is desired, for example, upon application of tension to a cable extending within the inner catheter 202 for recapture purposes, the stop 209 limits the inner catheter 202 axial movement with respect to the telescoping catheter 10 and limits the inner catheter from being in compression and prevents buckling. In one embodiment, the stop 209 is ring-shaped and extends from the outer surface of the inner catheter and can have an outer diameter that is slightly larger than the inner diameter of the tubular segment 22. Alternatively, the stop 209 can be a protrusion selectively extending proximal to the valve capsule or a thickening of the outer surface of the inner catheter proximal to the valve capsule 208. Other suitable embodiments of the stop 209 suitable to block the telescoping catheter 10 from extending past the stop 209 along the inner catheter 202 are also acceptable. The telescoping catheter 10 provides axial stiffness to that of the inner catheter 202 and works to decrease or prevent buckling without use of a mandral, for example, when the valve capsule 208 is retracted proximally over the valve (not shown). In one embodiment, the telescoping and rotational movement of the tubular segments 18, 20, 22 of the telescoping catheter 10 can be automated and operated by a motor instead of manually, if desired.

Although three tubular segments 18, 20, 22 are illustrated and described, the telescoping catheter 10 can include any number of tubular segments as appropriate to achieve the desired extended length and rigidity and is not limited to two or three segments. Factor that may influence the quantity may include the desired extended length of the telescoping catheter, the desired rigidity, and the thickness of material used, for example. The length of the tubular segments can also be varied in consideration with the above factors. Further, the tubular segments of the outer catheter can be of varying stiffness. In one embodiment, the tubular segments 18, 20, 22 can be approximately 18" (inches) long for a combined extended length of 3' to 5' (feet). The telescoping catheter 10, as well as the catheter assembly 200, can be formed by three-dimensional (3D) printing or any other conventional method. In one embodiment, the tubular segments are formed of Nylon 12 having a wall thickness of 0.010 or 0.015 inch wall thickness and the connectors are formed of polycarbonate. Other materials and thicknesses are also acceptable.

Although the present disclosure has been described with reference to preferred embodiments, workers skilled in the art will recognize that changes can be made in form and detail without departing from the spirit and scope of the present disclosure.

What is claimed is:

1. A catheter system, comprising:
   a prosthetic valve;
   an outer catheter member having an outer catheter member proximal end, an outer catheter member distal end, and a passageway extending between the outer catheter member proximal end and the outer catheter member distal end, the outer catheter member comprising a first tubular segment telescopingly received within a second tubular segment, the first tubular segment having a first proximal end, the outer catheter member further including a first connector disposed around an exterior surface of the first proximal end, and the second tubular segment having a second distal end, the outer catheter member including a second connector at the second distal end, wherein the first connector is mateable with and positioned within the second connector to maintain the first and second tubular segments in an extended position;
   an inner catheter slidably received within the outer catheter member and passed through the outer catheter member distal end and the outer catheter member proximal end so as to extend distally out of the outer catheter member, the inner catheter being configured to support the prosthetic valve at a location distal with respect to the outer catheter member;

a capsule coupled to a distal end portion of the inner catheter, wherein the prosthetic valve is contained within the capsule, wherein a proximal end of the capsule is distally spaced from the outer catheter member distal end with the outer catheter member in the extended position; and a handle coupled to the outer catheter member proximal end, the inner catheter slidably received within the handle.

2. The catheter system of claim 1, wherein at least one of the first and second tubular segments includes a first indicator that signifies when the first and second tubular segments are in the extended position.

3. The catheter system of claim 2, wherein the first indicator is a marking.

4. The catheter system of claim 2, wherein the first indicator signifies that the first and second tubular segments are in the extended position by way of friction created by a protrusion on one of the first and second tubular segments interlocking within a complimentary void in the other of the first and second tubular segments.

5. The catheter system of claim 2, wherein the first tubular segment includes the first indicator and the second tubular segment includes a second indicator; wherein alignment of the first and second indicators signifies when the first and second tubular segments are in the extended position.

6. The catheter system of claim 5, wherein the first indicator and the second indicator are markings.

7. The catheter system of claim 2, wherein the first indicator is provided on an exterior surface of at least one of the first and second tubular segments.

8. The catheter system of claim 2, wherein the first indicator includes a tactile indicator.

9. The catheter system of claim 8, wherein the first indicator also includes a visual indicator.

10. The catheter system of claim 1, wherein the first tubular segment has a first length from the first proximal end of the first tubular segment to a first distal end of the first tubular segment, the first length being greater than a second length from a second proximal end of the second tubular segment to the second distal end of the second tubular segment.

11. The catheter system of claim 1, wherein the first connector is slidably and rotatably mateable with the second connector.

12. The catheter system of claim 1, wherein the first connector includes a first sleeve affixed to the first tubular segment and the second connector includes a second sleeve affixed to the second tubular segment.

13. The catheter system of claim 1, further comprising a stop located on the inner catheter, outside of and distal to a distal-most end of the outer catheter member, wherein the stop limits axial movement of the inner catheter with respect to the outer catheter member, wherein the stop is positioned between the capsule and the outer catheter member.

14. The catheter system of claim 1, wherein the first tubular segment and the second tubular segment each have a wall thickness of 0.010 to 0.015 inches.

15. The catheter system of claim 1, wherein, with the outer catheter member in the extended position, the capsule is configured to be retracted proximally over the prosthetic valve to recapture the prosthetic valve.

16. A catheter system, comprising:
a prosthetic valve;
an outer catheter member having an outer catheter member proximal edge, an outer catheter member distal edge, and a passageway extending between the outer catheter member proximal edge and the outer catheter member distal edge, the outer catheter member comprising a first tubular segment telescopingly received within a second tubular segment, the first tubular segment having a first proximal end, the outer catheter member further including a first connector disposed around an exterior surface of the first proximal end, and the second tubular segment having a second distal end, the outer catheter member including a second connector at the second distal end, wherein the first connector is mateable with and positioned within the second connector to maintain the first and second tubular segments in an extended position;
an inner catheter slidably received within the outer catheter member such that the inner catheter extends distally out of the outer catheter member with the outer catheter member in the extended position, the inner catheter being configured to support the prosthetic valve at a location distal with respect to the outer catheter member with the outer catheter member in the extended position;
a capsule coupled to a distal portion of the inner catheter, wherein the prosthetic valve is contained within the capsule, wherein a proximal edge of the capsule is distally spaced from the outer catheter member distal edge with the outer catheter in the extended position; and
a handle coupled to the outer catheter member, the inner catheter slidably received within the handle.

* * * * *